(12) United States Patent
Chan

(10) Patent No.: US 7,588,141 B1
(45) Date of Patent: Sep. 15, 2009

(54) POCKET CASE FOR STORING AND DISPENSING PERSONAL ITEMS

(76) Inventor: Kevin Chan, 6 Honeyman Rd., Lebanon, NJ (US) 08823

( * ) Notice: Subject to any disclaimer, the term of this patent is extended or adjusted under 35 U.S.C. 154(b) by 0 days.

(21) Appl. No.: 12/148,881

(22) Filed: Apr. 23, 2008

(51) Int. Cl.
*B65D 85/14* (2006.01)
(52) U.S. Cl. ............... 206/69; 206/37; 206/459.1
(58) Field of Classification Search ......... 206/37, 206/39, 39.3, 39.4, 69, 459, 459.1; 221/52, 221/56, 59; 312/61, 71
See application file for complete search history.

(56) References Cited

U.S. PATENT DOCUMENTS

| | | | | | |
|---|---|---|---|---|---|
| 1,337,178 | A | * | 4/1920 | Fillmore | 206/69 |
| 4,045,102 | A | * | 8/1977 | Austin | 206/39 |
| 5,316,019 | A | * | 5/1994 | Jones | 206/69 |
| 5,564,431 | A | * | 10/1996 | Seward | 206/69 |
| 5,638,949 | A | * | 6/1997 | Jones | 206/69 |

\* cited by examiner

*Primary Examiner*—Luan K Bui
(74) *Attorney, Agent, or Firm*—Horst M. Kasper

(57) ABSTRACT

A pocket sized case for storing and dispensing condoms wherein a plurality of packaged condoms can be stored and dispensed without risk of breakage.

3 Claims, 3 Drawing Sheets

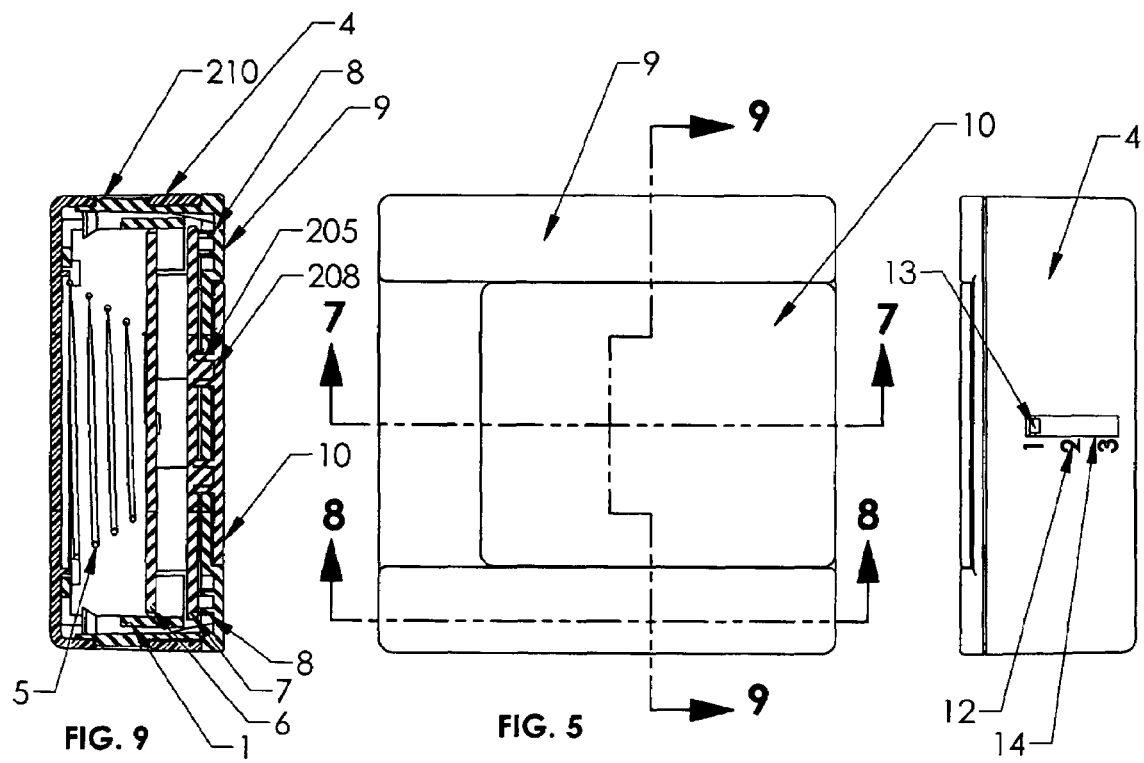
FIG. 9
FIG. 5
FIG. 6
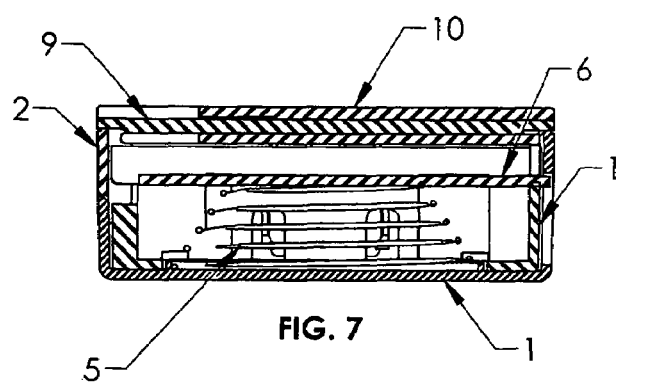
FIG. 7
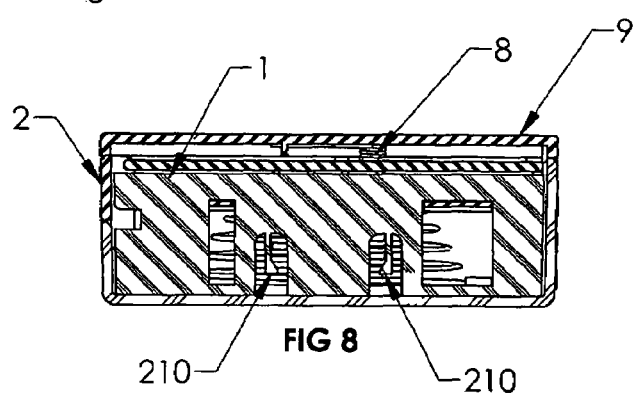
FIG 8

POCKET CASE FOR STORING AND DISPENSING PERSONAL ITEMS

FIELD OF THE INVENTION

This invention is directed toward portable pocket sized cases for storing and dispensing small personal items such as packages of condoms. In each case, a plurality of packages of condoms can be stored and dispensed without risk of breakage or the like. This case also preserves and protects each individual stored condom package from inappropriate usage or misusage.

BACKGROUND OF THE INVENTION

Small packages of condoms are often carried in purses, wallets and the like. However, when carried for a period of time, such stored packages may peal and break, destroying the freshness or even the effectiveness of the condom.

The present invention provides a new and improved pocket sized case wherein a plurality of packages of condoms can be stored and dispensed without risk of breakage or the like. This case also preserves and protects each individual stored condom package from inappropriate usage or misusage while providing privacy for the person or persons using the case.

SUMMARY OF THE INVENTION

A pocket case for storing and dispensing personal items employs a first set of four interconnected vertical panels disposed at right angles to each other, secured to a flat bottom base disposed below an upper cover and enclosing a hollow interior space. One of the panels contains an upper horizontal recess for receiving a pivoted horizontal door.

A second set of vertical interconnected vertical panels are disposed at right angles to each other and disposed below the upper cover. The second set is fitted within and adjacent the first set with the base of the second set disposed above and adjacent to the bottom of the first set and having a circular opening. One of the second set panels has an opening supporting the horizontal door in registration with the horizontal recess of the first set panels.

An upwardly tapered horizontal coil spring is disposed in the circular opening with its base engaging the base of the first set panels. A horizontal spring plate is spaced within the two sets and movable up and down within the interior space below the cover and engages the top of the coil spring. The plate can be locked in any horizontal position by spring locking cams which can be manually engaged and disengaged. The cover has a top mounted slide button.

A dispensing plate is disposed in said space above the spring plate and below the cover and has a push rib extending downward therefrom. Spring means [two oppositely disposed slide button springs] connect the dispensing plate and the cover. The cover has slots and the slide button has a slide boss which extends through said slots and engages the dispensing plate.

Condoms can be loaded into and dispensed from this structure as described in the description which follows.

BRIEF DESCRIPTION OF THE DRAWINGS

FIG. 3 is a detail view contained in a circle of certain parts of the case.
FIG. 4 is an enlarged view of the structure shown in FIG. 3.
FIG. 5 is a top plan view of the case.
FIG. 6 is a view of the counter mechanism.
FIG. 7 is a view along line 7-7 in FIG. 5.
FIG. 8 is a view along line 8-8 in FIG. 5.
FIG. 9 is a view along line 9-9 in FIG. 5.

DETAILED DESCRIPTION OF PREFERRED EMBODIMENT

Figure 1:
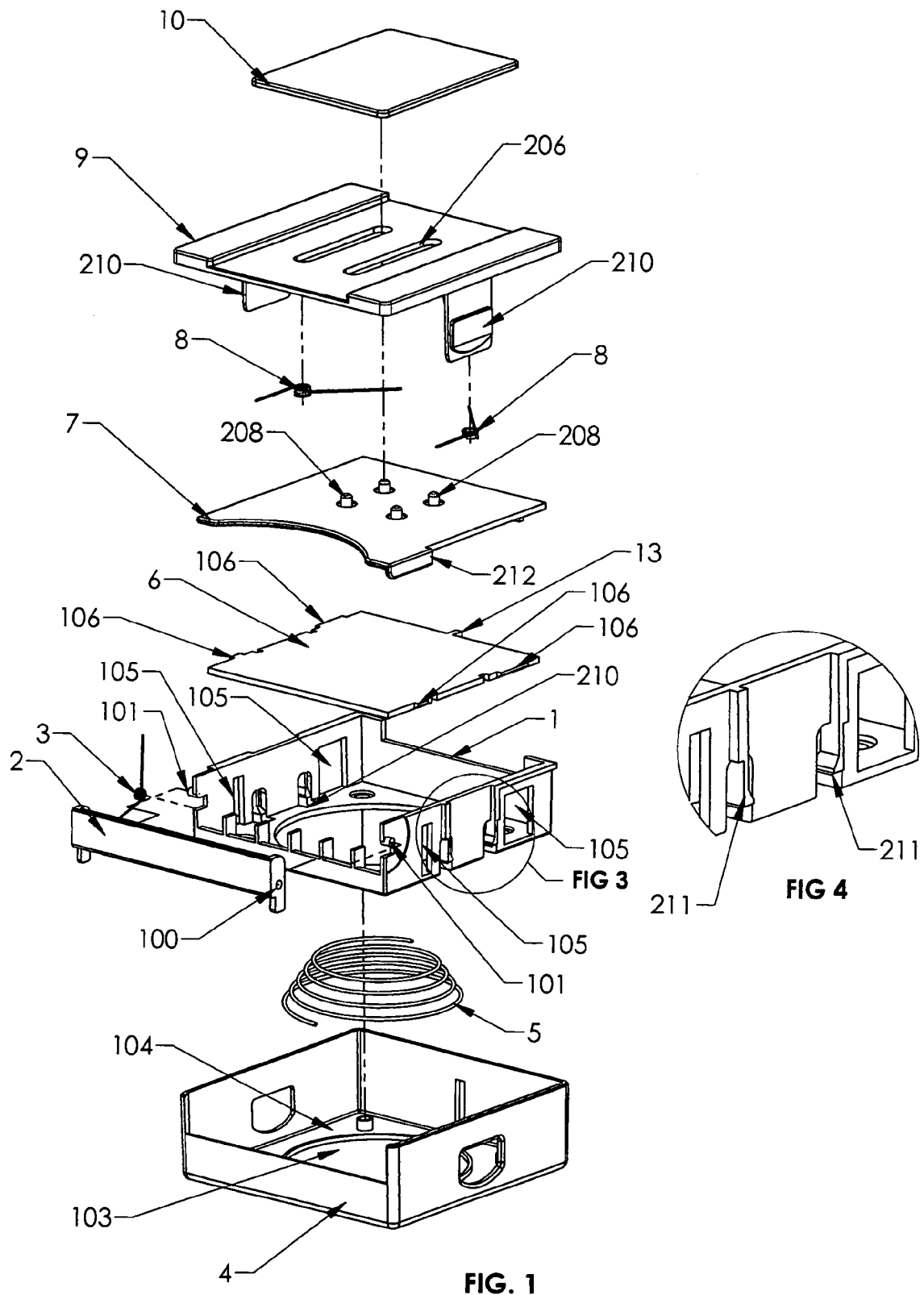
FIG. 1 is an exploded front view of the case.
Figure 2:
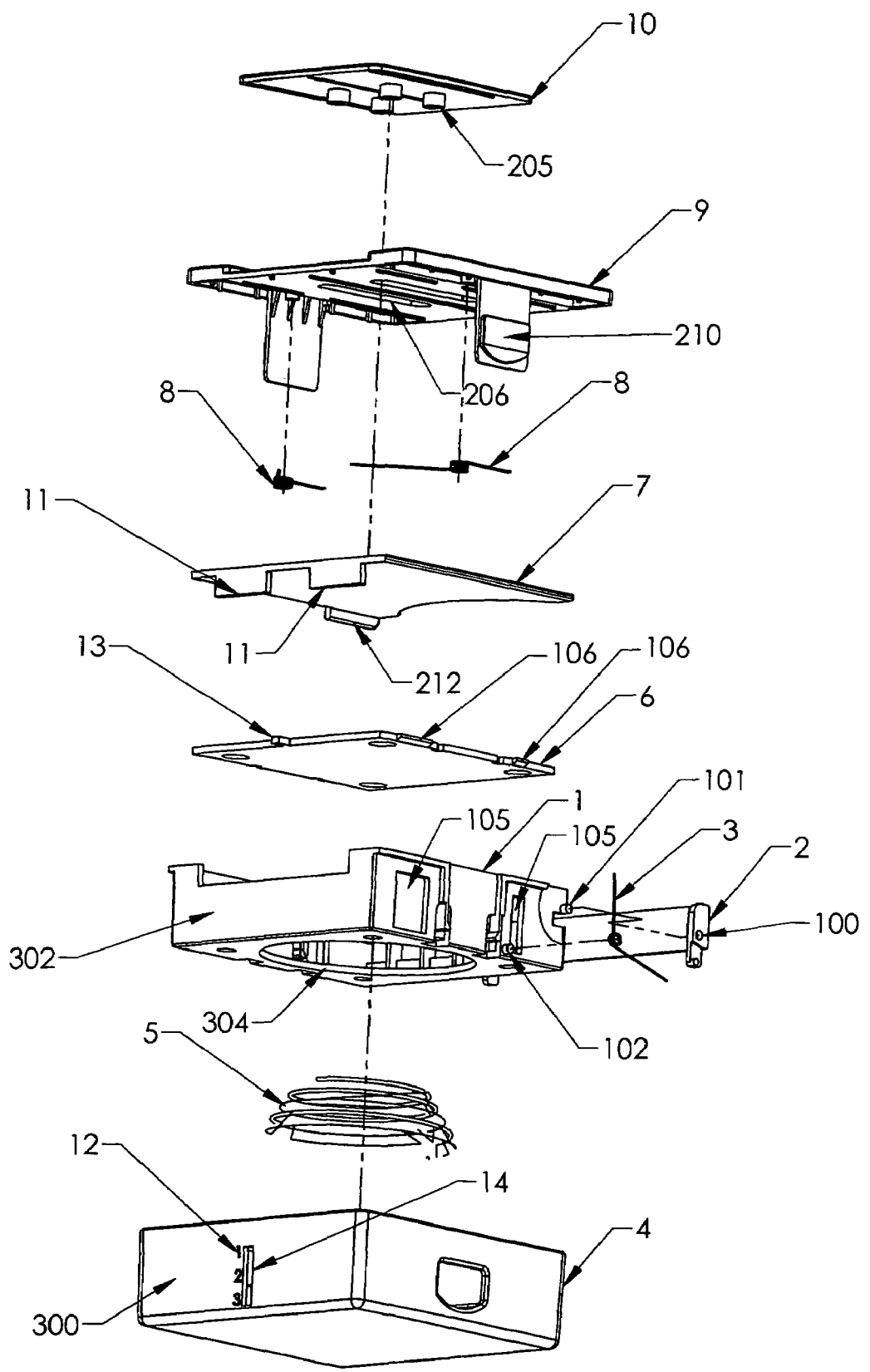
FIG. 2 is an exploded back view of the case.

A pocket case for storing and dispensing personal items employs a first set identified generally at 300 of four interconnected vertical panels disposed at right angles to each other, secured to a flat bottom base 1, disposed below an upper cover 9 and enclosing a hollow interior space. One of the panels 4 contains an upper horizontal recess for receiving a pivoted horizontal door 2.

A second set identified generally at 302 of vertical interconnected vertical panels are disposed at right angles to each other and disposed below the upper cover. The second set is fitted within and adjacent the first set with the base of the second set disposed above and adjacent to the bottom of the first set and having a circular opening 304. One of the second set panels has an opening supporting the horizontal door in registration with the horizontal recess of the first set panels.

An upwardly tapered horizontal coil spring 5 is disposed in the circular opening with its base engaging the base of the first set panels. A horizontal spring plate 6 is spaced within the two sets and movable up and down within the interior space below the cover and engages the top of the coil spring. The plate can be locked in any horizontal position by spring locking cams 211 which can be manually engaged and disengaged;

The cover 9 has a top mounted slide button 10. A dispensing plate 7 is disposed in said space above the spring plate and below the cover and having a push rib 212 extending downward therefrom. Spring means [two oppositely disposed slide button springs 8] connect the dispensing plate and the cover. The cover has slots 206 and the slide button has a slide boss 205 which extends through said slots and engages the dispensing plate.

Loading

Remove cover (9) by depressing the two finger tabs (210) on each side of the case and pulling up on the cover. Push down on the spring plate (6) until it is locked at the bottom loading position by the spring plate locking cams (211). Load the condoms into the case on top of the spring plate (6). Insert the cover finger tabs (210) into the case and press until the finger tabs (210) lock in. When the finger tabs (210) lock in they also spread the dispensing plate locking cams (211) releasing the spring plate allowing the Dispensing spring (5) to apply pressure to hold the condom against the dispensing plate (7) ready for use. The count indicator (13) passes through the slot (14) in the Base (4) and lines up with the numbers (12) on the Base (4) to show how many condoms are in the dispenser.

Dispensing

To dispense the condoms, the Slide button (10) is pushed forward depressing the Slide button springs (8) and driving the Dispensing plate (7) which drives the condom through the Door (2) that is spring load by the door spring (3) The door is pushed open by a door cam (212) and the condom is dispensed through the door (2) by means of the Push rib (11) of the Dispensing plate (7). For each condom removed the elevation of the Spring plate (6) changes position applying pressure to the next condom ready for use.

The rigidness of the package provides robust storage and a discrete package for the condoms. The condoms are kept secure from being damaged or punctured from other objects in hand bags and the like.

What is claimed is:

1. A pocket case for storing and dispensing personal items, said case comprising:
   a first set of four interconnected vertical panels disposed at right angles to each other, secured to a flat bottom base and disposed below an upper cover, said panels enclosing a hollow interior space, one of the panels containing an upper horizontal recess for receiving a pivoted horizontal door;
   a second set of vertical interconnected vertical panels disposed at right angles to each other and disposed below the upper cover, the second set having a flat bottom base containing a circular opening, said second set fitted within and adjacent the first set with the base of the second set disposed above and adjacent to the bottom of the first set and having the circular opening, one of the second set panels having an opening supporting a horizontal door in registration with the horizontal recess of the first set panels;
   an upwardly tapered horizontal coil spring disposed in the circular opening with its base engaging the base of the first set panels;
   a horizontal spring plate spaced within the two sets and movable up and down within the interior space below the cover and engaging the top of the coil spring, the plate can be locked in any horizontal position by spring locking cams which can be manually engaged and disengaged;
   said cover having a top mounted slide button;
   a dispensing plate disposed in said space above the spring plate and below the cover and having a push rib extending downward therefrom; and
   spring means connecting the dispensing plate and the cover.

2. The case of claim 1 wherein the cover has slots and the slide button has a slide boss which extends through said slots and engages the dispensing plate.

3. The case of claim 2 provided with mechanical means to display a count of the number of individual condom packages stored in or removed from the case.

* * * * *